US006306425B1

(12) United States Patent
Tice et al.

(10) Patent No.: US 6,306,425 B1
(45) Date of Patent: Oct. 23, 2001

(54) INJECTABLE NALTREXONE MICROSPHERE COMPOSITIONS AND THEIR USE IN REDUCING CONSUMPTION OF HEROIN AND ALCOHOL

(75) Inventors: Thomas R. Tice, Birmingham; Jay K. Staas, Alabaster; Teresa M. Ferrell, Vestavia Hills, all of AL (US)

(73) Assignee: Southern Research Institute, Birmingham, AL (US)

( * ) Notice: Subject to any disclaimer, the term of this patent is extended or adjusted under 35 U.S.C. 154(b) by 0 days.

(21) Appl. No.: 09/545,064

(22) Filed: Apr. 7, 2000

Related U.S. Application Data

(60) Provisional application No. 60/128,477, filed on Apr. 9, 1999.

(51) Int. Cl.[7] .............................. A61F 2/00; A61K 9/00; A61K 9/14; A61K 47/30
(52) U.S. Cl. ..................... 424/426; 424/400; 424/486; 424/489; 514/872; 514/811; 514/772.3; 514/812; 514/964
(58) Field of Search .................... 424/426, 423, 424/425, 486, 449, 451, 489, 501, 502; 514/772.3, 810

(56) References Cited

U.S. PATENT DOCUMENTS

| | | | |
|---|---|---|---|
| 3,773,919 | 11/1973 | Boswell et al. | 424/19 |
| 3,887,699 | 6/1975 | Yolles | 424/19 |
| 4,568,559 | 2/1986 | Nuwayser et al. | 427/3 |
| 4,623,588 | 11/1986 | Nuwayser et al. | 428/402.24 |
| 4,874,612 | 10/1989 | Deasy | 424/425 |
| 4,897,267 | 1/1990 | Bontemps et al. | 424/422 |
| 4,897,268 | 1/1990 | Tice et al. | 424/422 |
| 4,902,515 | 2/1990 | Loomis et al. | 424/486 |
| 4,981,696 | 1/1991 | Loomis et al. | 424/486 |
| 5,100,669 | 3/1992 | Hyon et al. | 424/426 |
| 5,407,609 | 4/1995 | Tice et al. | 264/46 |
| 5,486,362 | * 1/1996 | Kitchell et al. | 424/426 |
| 5,736,152 | * 4/1998 | Dunn | 424/426 |
| 5,945,115 | 8/1999 | Dunn et al. | 424/422 |

OTHER PUBLICATIONS

Falk, et al., *J. Controlled Release* (1997), 44(1):77–85.
Yolles, et al. *Acta Pharmaceutica Suecica* (1976), 13(32).
Jalil and Nixon., *J. Microencapsulation* (1990), 7(3):297–325.
Sharon and Wise, *NIDA Res Monogr* (1981), 28:194–213.
Schwope, et al., *Life Sciences* (1975), 17(12):1877–85.
Woodland, et al., *J. Med Chem* (1973), 16(8):897–901.

* cited by examiner

*Primary Examiner*—Blessing Fubara
(74) *Attorney, Agent, or Firm*—Barbara Rae-Venter; Jennifer Wahlston; Rae-Venter Law Group P.C.

(57) ABSTRACT

An injectable slow-release naltrexone formulation is provided comprising naltrexone in a poly(D,L-lactide) matrix with a small amount of residual ethyl acetate. Upon intramuscular injection of the composition, naltrexone is released in a controlled manner over an extended period of time. The composition finds use in the treatment of heroin addicts and alcoholics to reduce consumption of the abused substances.

26 Claims, No Drawings

INJECTABLE NALTREXONE MICROSPHERE COMPOSITIONS AND THEIR USE IN REDUCING CONSUMPTION OF HEROIN AND ALCOHOL

CROSS REFERENCE TO RELATED APPLICATIONS

This application claims priority to provisional application serial No. 60/128,477, filed Apr. 9, 1999, which disclosure is herein incorporated by reference.

INTRODUCTION

Background

The disease of substance abuse remains a scourge on society. As it becomes more evident that there is a substantial genetic contribution to becoming addicted, helping addicted individuals to terminate their dependency or at least achieve a level of becoming a functional member of society, rather than treating substance abuse as a moral issue, has become increasingly accepted policy. Various programs have been put in place in the public and private sectors. In the private sectors, there are such organizations as Alcoholics Anonymous and Narcotics Anonymous, which play an important role in psycho-social support. In addition there are many private clinics which serve to provide both psycho-social support and medicinal support, using the somewhat limited repertoire of drugs which are available. In the public arena, there are the extensive programs to bring to the attention of young people and parents the hazards of substance abuse and discourage the young people from embarking on drug use. Also, there are the methadone programs, which are primarily public supported.

The number of substance abusing subjects in the United States is quite staggering. There are estimated to be about 15 million people who abuse alcohol, about 1.3 million who abuse cocaine in its many manifestations, about 0.8 million who abuse amphetamines and about 0.5–0.8 million who abuse heroin, in addition to the use of other drugs, such as the psychedelic drugs. Efforts to reduce the numbers of scheduled substances and alcohol users have been continuous and relatively unavailing. Those subjects who have entered programs have had a dismal record of relapse, so that only a small proportion of the people who do enter programs and are retained in the programs remain clean long after the completion of the program.

One significant factor in lack of retention and relapse is compliance. A repetitive act, such as taking a pill daily, is not a simple matter, even where the subject has no qualms about taking the pill. With the substance abuser, who may have physiological and emotional needs for the abused substance, the sustaining of the therapeutic routine is substantially more difficult. Therapeutic techniques, which require perseverance on the part of the subject, decrease the likelihood of success of the treatment. It is therefore of great importance to be able to reduce the level of involvement of the subject where medicinal treatments are involved, particularly treatments, which may involve frequent scheduling, monitoring of compliance, and sustaining a particular regimen.

In order to reduce the vicissitudes of compliance, there have been efforts to provide sustained-release methodologies. These have involved pumps, patches, depots and the like. Where the release implement is accessible to the subject, there is always the temptation to remove the implement during a craving episode. This opportunity, which may be an indication of will power, nevertheless, puts the subject at risk that succumbs to the temptation. By providing for a slow-release medicament, which is introduced into the body, the temptation is avoided and the drug is released in accordance with a predetermined schedule over an arranged period of time. One can have implantable rods, which are introduced surgically and must be removed surgically or microspheres, which are injectable and are devised to release the drug over an extended period of time in a controlled manner.

Various slow-release microspheres (or microparticles) have been developed for a variety of drugs, a few have been commercialized. There are many constraints on a satisfactory slow-release injectable formulation: the release of the drug must be over an extended period of time; during the time of treatment, the level of drug maintained in the subject must be an effective level, without reaching any hazardous level; the drug must be released slowly without a catastrophic dumping of the drug; the polymeric matrix used for the microspheres must be biocompatible and biodegradable; any residual chemicals must be below the maximum acceptable level; the microspheres must be small and capable of being delivered by a syringe with a needle which is acceptable to patients; the results must be reproducible, which requires that the process can be accurately controlled and is not unduly sensitive to minor changes in conditions; the injectable formulation must be capable of being sterilized; the metabolites that are produced must be acceptable levels; as well as other characteristics which may be general or specific to the particular medicament. The properties of the microspheres are sensitive to many properties of the drug and matrix, as well as the selection of the process and the conditions under which the microspheres are prepared and subsequently processed.

BRIEF DESCRIPTION OF THE PRIOR ART

Krantzler, et al., Alcoholism: Clin and Exp Res 1998, 22:1074–1079 report the treatment of alcoholics with a slow-release naltrexone particle injectable formulation. A number of studies were carried out by Reuning's laboratory concerning naltrexone and its use in a slow-release form: Reuning, et al., NIDA Re: Monograph Series, January 1976, (4) p43–5; Reuning et al., J. Pharmacokinet Biopharm, August 1983, 11 (4), p369–87; Reuning, et al., Drug Metab Dispos November–December 1989, 17(6) p583–9; MacGregor et al., J. Pharm Pharmacol, January 1983, 35(1) p38–42; Reuning et al., NIDA Res Monograph Series 1980, 28, p172–84. See also, Schwope et al., NIDA Res Monograph Series, 1975, (4), p13–8; Yolles et al., J Pharm Sci Febuary 1975, 64(2) p348–9; Thies, NIDA Res Monograph Series, 1975 (4), p19–20; Schwope et al., NIDA Res Monograph Series, January 1976, 4, p13–18; Chiang et al., Clin Pharmacol Ther Nov. 1984 36(5) p704–8; Pitt et al., NIDA Res Monograph Series 1981, 28, p232–53; Chiang et al., Drug Alcohol Depend (SWITZERLAND), September 1985, 16 (1) p1–8; Yoburn et al., J. Pharmacol Exp Ther, April 1986, 237 (1) p126–130; Cha and Pitt, J. Control Release, 1989, 8(3), p259–265; Yamaguchi and Anderson, J. Control Release, 1992, 19(1–3), p299–314.

The use of naltrexone in the treatment of alcoholism is described in O'Malley et al., Psychiatric Annals, November 1995, 11, p681–688, as well as numerous other publications.

Patents of interest include U.S. Pat. Nos. 4,568,559; 4,623,588; 4,897,267; and 5,486,362. U.S. Pat. No. 5,407,609 describes a process applicable to the process employed in the subject invention.

The use of polylactide in the preparation of drug containing microspheres is described in Benita et al., J Pharm Sci, December 1984, 73(12) p1271–4; Speniehauer et al., ibid, August 1986, 75(8), p 750–5; and Nihant et al., October 1994, 11(10), p1479–84.

SUMMARY OF THE INVENTION

Injectable, slow-release naltrexone formulations are provided comprising a therapeutically effective amount of naltrexone released over an extended period of time and a matrix consisting of the polymer poly(D,L-lactide). The microspheres are under 100 μm in diameter and can be readily injected intramuscularly. Different release profiles are obtained depending upon the molecular weight of the polymer, molecular-weight homogeneity of the polymer, matrix size of the microspheres, and the weight percentage of naltrexone. The microspheres are prepared by solvent extraction of a oil-in-water emulsion, the dispersed oil phase being an organic solution of naltrexone and the polymer.

DESCRIPTION OF THE SPECIFIC EMBODIMENTS

Injectable, slow-release naltrexone formulations are provided for use in the treatment of alcoholics and heroin addicts and such other indications for which naltrexone has been found to be efficacious. Small sterilized particles, microspheres, are provided which can pass through a syringe needle and be administered intramuscularly and remain at the site of injection for an extended period of time, while continuously releasing and maintaining a therapeutically effective amount of naltrexone for at least about 28 days. The release profile is found to be sensitive to the amount of naltrexone in the microspheres, the use of the free base as compared to the salt and the inherent viscosity and homogeneity (molecular-weight profile) of the poly(D,L-lactide). The release profile appears to be less sensitive to the conditions under which the microencapsulation process is operated, the size distribution of the microspheres, as long as the composition substantially consists of particles in the range of 20 to 100 μm, and the amount of polymer solvent retained, so long as the amount of polymer solvent is below about 3 weight %.

The microspheres as observed by SEM are substantially uniform with the drug dispersed throughout the matrix. The microspheres have less than about 3 weight % of ethyl acetate, the organic solvent used in the preparation of the microspheres. The content of naltrexone in the microspheres is from 5 to 50 weight % and may vary in range depending upon the inherent viscosity of the poly(D,L-lactide) making up the microsphere polymer matrix. The inherent viscosity of the polymer is in the range of about 0.3 to 1.2 dL/g (Capillary viscometry method, chloroform, polymer concentration of 0.5 g/dl, 30° C.). Where the matrix has an inherent viscosity in the range of about 0.3–0.4 dL/g, the amount of naltrexone will be in the range of about 5 to 45 weight %, usually 10 to 40 weight %, particularly 10 to 30 weight %. While when the inherent viscosity is in the range of about 1.0–1.2 dL/g, usually 1.0–1.1 dL/g, the amount of naltrexone will be in the range of about 35 to 50 weight %, usually 35 to 45 weight %. For the most part, polymers having an inherent viscosity in the range of 0.45 to 0.95 dL/g will not be employed. Mixtures of the polymers and/or microspheres may be used so as to deliver the desired amount of naltrexone over the desired time period. Thus, when mixing two polymers (prior to microencapsulation) having different inherent viscosities, the weight % of two different polymers may range from 1:99 to 99:1, more usually 10:90 to 90:10, where the polymer with the lower inherent viscosity (i.e., the lower-molecular-weight polymer will be in lesser amount than the polymer with the higher inherent viscosity (the higher-molecular-weight polymer)). Similarly, naltrexone microspheres made with a low-molecular-weight polymer may be mixed with microspheres made with a higher-molecular-weight polymer, where the drug loading (weight % of naltrexone in the microsphere formulation) may vary as to the two or more microspheres mixed together. With two different microsphere formulations, the mixture will have a weight ratio in the range of 5:95 to 95:5, where the microspheres made with the lower-molecular-weight polymer will usually be present in from about 10 to 65 weight %.

Greater than about 90 weight % of the microspheres will have a diameter in the range of about 20 to 100 μm and less than about 5 weight % will have a diameter greater than about 100 μm.

To reduce agglomeration, the microspheres may be coated with an antiagglomerating agent, such as mannitol, which will be employed in less than about 10 weight %, usually less than about 5 weight %, and may be less than about 2 weight %, of the microspheres.

Desirably, the microspheres release naltrexone over a period of at least 4 weeks, where the area under the curve in monitoring the plasma level of naltrexone in human subjects is less than about 40% in any one week period and at least about 10%, preferably at least about 12%. Generally, the proportion in at least two of the weeks, preferably 3 of the weeks is not greater than 25%, usually not greater than 20%. Desirably, at least about 75%, preferably at least about 80% and not more than about 95% of the naltrexone, as determined by the area under the curve, is released in the first 4 weeks. The area under the curve is determined by a standard pharmacokinetics computer program entitled WinNonlin Professional (version 2.1, Pharsight, Inc., Mountain View, Calif.).

The microspheres are formulated in an appropriate vehicle to provide from about 150–350 mg of naltrexone, usually 250 to 350 mg of naltrexone, particularly 300±15 mg of naltrexone, for an administration. The vehicle may be sterile water, phosphate buffered saline, or other conventional vehicle for administering the microspheres. Additives may be present to reduce adhesion of the microspheres, diminish discomfort from the injection, reduce edema, itching, bumps or other discomfort. Conveniently, mannitol may be present in about 2 to 10 weight % of the vehicle, particularly 4 to 7 weight % of the vehicle. Other physiologically acceptable additives may include nonionic detergents, e.g. Tween, polysorbate, etc., if present, will be present in from about 0.05 to 0.2 weight % of the vehicle, viscosity enhancing agents, e.g. carboxymethylcellulose, in the range of about 0.1 to 1 weight % of vehicle, and other conventional additives, as appropriate. The amount of vehicle will generally be in the range of about 1.5 to 5 mL, usually 2 to 4 mL, particularly 2 to 3 mL, where the lower amounts will generally involve multiple injections, e.g. 2. The microspheres are dispersed in the vehicle immediately before use. Generally, the microspheres will be stored after sterilization in a sterile vial with a septum, where the microspheres may be mixed with the vehicle and then withdrawn into a syringe. Usually, the needle will not be of greater inner diameter than about 18 gauge. With multiple injections per administration, they may be at the same, adjacent or removed sites.

The microspheres are prepared by the microencapsulation process substantially as described in U.S. Pat. No. 5,407,609. The process is an emulsion-based process which involves the preparation of an emulsion comprising an aqueous continuous phase (water and a surfactant and/or thickening agent) and a hydrophobic dispersed phase (polymer solvent, polymer and drug) Shortly after formation of the emulsion, the polymer solvent is extracted into an aqueous extraction phase. After a sufficient amount of polymer solvent is extracted to harden the microspheres, the microspheres are collected on sieves and washed to remove any surfactant remaining on the surface of the microspheres. The microspheres are then air dried at room temperature, or dried by lyophilization or by other convenient drying processes.

For the preparation of the subject microspheres, the dispersed phase (organic solution) contains about 1 to 10 weight % naltrexone and about 1 to 20 weight % polymer dissolved in ethyl acetate. The continuous phase is an aqueous solution of about 1 to 10 weight % of poly(vinyl alcohol) and 1 to 7 weight % ethyl acetate. The extraction phase is water. Generally, the amount of naltrexone employed will be from about 20 to 50 weight % in excess of the final amount of naltrexone in the microparticles. Temperatures may be ambient, generally being from about 15 to 30° C.

After the microspheres have been collected and dried, they may be stored at ambient temperatures, particularly in the range of about 0 to 20° C. in an oxygen free and water free environment or divided into aliquots into appropriate containers and sterilized. Various methods of sterilization may be employed, gamma radiation being convenient.

A relatively simple apparatus may be employed to fabricate the microspheres. Using storage containers to hold the different liquids, tubing, pumps, valves and a homogenizer, the system is readily assembled. In addition, various monitoring devices may be included, such as flow meters, temperature monitors, particle size monitors, etc. The organic solution is pumped into a first tube, which fits into the homogenizer. Likewise the aqueous solution (to be the continuous phase) is pumped into the second tube which also fits into the homogenizer. By controlling the rate of flow of the two streams in the tubes connecting to the homogenizer, the ratio of the two streams can be controlled, as well as the residence time in the homogenizer. The effluent from the homogenizer (an oil-in-water emulsion) exits through a third tubing containing flowing water. The water extracts the polymer solvent ethyl acetate from the emulsion droplets to form microspheres. Again, the ratio of flow rates controls the amount of emulsion and water introduced into the third tubing. The length of the third tubing and the rate of flow of the combined streams control the residence time of the water-extraction step. The microspheres are then segregated by size by passing them through two or more sieves, which reject microspheres outside the desired size range.

The primary application for the subject formulations is as an intramuscular injectable, although subcutaneous injections may also be used. The subject will normally be a substance abuser, such as alcohol and heroin, but the subject compositions may be used for other indications, such as obesity. The appropriate amount of the subject formulation is directly injected into a convenient site, e.g. gluteus. Thereafter, the subject may be monitored for naltrexone plasma concentration to ensure that the amount is in the therapeutic range of at least about 1 ng/mL, preferably at least about 2 ng/mL. When the naltrexone plasma concentration falls below the therapeutic range, a subsequent injection may be made and this process repeated during the treatment period.

For heroin addicts, the subject will normally be detoxified by any one of a number of different ways, using buprenorphine, clonidine, naltrexone, etc. and checking with naloxone. A response to naloxone indicates that the subject has not been completely detoxified. It is also found that about 10% of the population that has been tested with oral naltrexone have adverse reactions, which may resolve themselves or exclude the use of naltrexone. In addition, there have been some reports of hepatotoxicity resulting from the use of naltrexone at high dosages, with the potential that high doses of the metabolite, 6β-naltrexol having hepatotoxicity, so that subjects who have compromised livers, e.g. subjects infected with hepatitis C, may be excluded from treatment. Otherwise, naltrexone has been found to be safe at administered levels in excess of the levels employed with the subject compositions. With alcoholics, once it has been determined that the subject does not respond adversely to naltrexone, the subject formulation may be injected into the subject. It is found that naltrexone serves to enhance the control of the alcoholic in the amount of alcohol consumed and the number of binges.

By having microspheres which have long-term releasing capability, that is, greater than 28 days, particularly greater than about 32 days, one can layer the administration, so that by giving injections in a periodic manner, one obtains an additive effect. In this manner, smaller doses may be administered after the first dose, because one continues to obtain release from the prior injected microspheres to which is added the release from the lately administered microspheres, or one can enjoy enhanced levels of the naltrexone without increasing the amount of the microspheres which are administered. By providing for microspheres that can continue to release at levels in excess of 1 ng/mL in blood, preferably in excess of 1.5 ng/mL in blood, more preferably in excess of 2 ng/mL in blood, greater than about 28 days after injection, frequently at least about 36 days, more frequently at least about 42 days. In this way protection is greatly enhanced, as the subject is continuously protected with a protective level of the naltrexone and one can provide levels of naltrexone which will inhibit response to a 50-mg challenge dose of heroin or an equivalent dose of a different drug, e.g. fentanyl.

The following examples are offered by way of illustration and not by way of limitation.

EXPERIMENTAL

The microencapsulation process involves microencapsulation by solvent extraction. Naltrexone anhydrous base, poly(D,L-lactide) and ethyl acetate are combined and added to the in-line homogenizer with water and surfactant. An emulsion is produced, additional water is added and the extraction process is initiated. The product, naltrexone microspheres, is dried by lyophilization in jars. Gamma sterilization at 2.5 Mrad exposure is used, and bioburden, bacteriostasis, and fungistasis are monitored.

The appropriate amount of dried, naltrexone microspheres are weighed into empty 5-cc vials, closed with rubber stoppers, sealed with aluminum seals and sealed into foil pouches for transport and sterilization. A vial containing 2 mL of diluent comprising 0.5% carboxymethyl cellulose, 0.1% polysorbate 80 and 5% mannitol is used to resuspend the microspheres. The suspension is drawn into a 3-cc syringe with an 18-gauge needle. The intramuscular injection is given immediately to prevent the microspheres from settling. The injection may comprise one or two injections of from 2 to 4 mL, usually not more than a total of 4 mL.

Size distribution is controlled such that 90 volume % of each batch is >40 μm and <90 μm. In vitro release characteristics are defined by % released over the first 72 hours at 37° C.

A description of the microencapsulation of naltrexone is included in the following sections.

Step 1: A 2.5 wt % solution of polymer is prepared by mixing ethyl acetate with poly(D,L-lactide), low molecular weight, in an 8-liter bioreactor flask equipped with a PTFE-coated stirring shaft. A minimum of 4 hours is required to completely dissolve the polymer. The weight of the polymer solution and its flask is measured and if needed, additional ethyl acetate is added to return the solution back to it's desired weight.

Step 2: A 2 wt % poly(vinyl alcohol) (PVA) solution is prepared by mixing PVA in sterile water, in 3 to 4 batches, and stirring at 90° C. Each batch is then allowed to cool to room temperature and then water is added back to adjust for evaporation loss. After a pre-filter integrity test of a Millipak 200-liter unit is successfully completed, the solutions are filtered and pooled in a 36-liter bioreactor flask. The flask and its contents are then weighed, 2.5 wt % ethyl acetate is added to the PVA solution and a motor driven PTFE impeller stirs the solution for a minimum of 30 minutes.

Step 3: For every 15 gm of drug product produced, a minimum of 8 liters of water is transferred to a 50-gallon stainless steel tank, covered and stored.

Step 4: The naltrexone dispersed phase solution is prepared by adding naltrexone to the polymer solution while stirring. The solution is stirred for a minimum of 1 hour until the naltrexone is dissolved.

Step 5: To set up the continuous microencapsulation equipment, the dispersion phase, continuous phase and extraction phase and pumps are calibrated to a specified flow rate, for example, 25 gm/min, 125 gm/min, and 2000 gm/min respectively to prepare Formulation F-1. The dispersion phase needle is then primed with dispersion phase solution and the dispersion phase pump flow rate is confirmed on a bypass setting. The extraction phase pump is then started and the extraction lines are filled and cleared of bubbles. The continuous phase pump is then turned on and PVA is allowed to flow into the extraction tubing. The homogenizer is then turned on and set to a stir rate of 650±20 rpm. The dispersion phase needle valve is then opened and the dispersion phase pump is turned on to allow dispersion phase solution to flow into the homogenizer chamber with the PVA solution. This is the start of the batch run. Following homogenization, the emulsion flows out of the in-line homogenizer and into the extraction line containing flowing water, which extracts ethyl acetate from the microspheres.

The aqueous suspension of microspheres is then collected into a 50-gallon stainless steel holding tank, equipped with a stir motor and impeller. The microspheres are stirred at 500±50 rpm until the tank is 25 to 50% full. The microsphere suspension is then moved through a RBF-12 Vorti-Sieve oscillating sieve deck containing a 125-$\mu$m and a 20-$\mu$m sieve in series, using a centrifugal pump. If the sieves become clogged, they are removed and replaced with a new set of clean sieves. The 20-$\mu$m sieve is then rinsed with water into the 80-gallon stainless steel washing bath tank and continuously stirred while the rest of the run is being collected. After the last of the dispersion phase solution passes into the homogenizer, the dispersion phase pump is stopped and the dispersion phase needle valve is closed off. This is the end of the batch run. The final amount of dispersion phase solution is then homogenized, extracted, and filtered though the sieves.

Water is then pumped across the sieves for 10 minutes to wash the microspheres. The microspheres on the 20-$\mu$m sieve are then rinsed into the 80-gallon stainless steel washing bath tank and continuously stirred at 500±50 rpm for a minimum of 3 hours. The microspheres are then passed through another RBF-12 Vorti-Sieve oscillating sieve decks containing a 125-$\mu$m and a 20-$\mu$m sieve in series, using a centrifugal pump. The microspheres on the 20-$\mu$m sieve are then transferred to a collection vessel by rinsing with water. Microspheres are diluted with water to make a 15% solids suspension based on estimated yield. The suspension is stirred continuously while dividing contents into one liter lyophilization flasks such that each flask contains an estimated 20 gm of microspheres. After lyophilization, microspheres are dry sieved through a 125-$\mu$m sieve. The microspheres are then weighed and distributed to amber glass bottles.

The bottles are then capped, sealed and packaged in plastic bags with silica gel desiccant. Bags are stored at 2 to 8° C.

After the microspheres meet the pre-defined acceptance criteria for core loading, size distribution, theoretical yield and residual ethyl acetate, they are packaged, as single doses, into 5-cc flint glass vials. The vials are then capped with PTFE-coated rubber stoppers, sealed with open top aluminum seals , labeled and sealed into individual foil pouches.

A guideline describing the detailed preparation and components of the kits is provided below.

1. Using an 18-gauge needle, draw 2.0 cc of diluent up into a 3 cc syringe and expel into a vial containing microspheres. Discard this needle and syringe.
2. Shake the vial vigorously for 30 seconds to suspend microspheres.
3. Place a new 18-gauge needle on a new 3-cc syringe.
4. Draw microsphere suspension into syringe while inverting vial.
5. Expel microspheres back into vial.
6. Repeat steps 4 and 5 two additional times.
7. Discard this needle and syringe.
8. Place a new 18-gauge needle on a new 3-cc syringe.
9. Draw microsphere suspension into syringe while inverting vial. Withdraw needle from vial.
10. Remove air bubbles from suspension and administer the dose as soon as possible to prevent settling of microspheres.

The following table indicates specific parameters for the preparation of the microspheres and the properties and performance of the microspheres in vitro and in vivo. In the in vivo study, dogs were injected intramuscularly with an 18-guage needle with about 2 mL of solution containing the microspheres at the weight indicated in the table. The plasma was monitored for naltrexone at the times indicated. For the in vitro study, microspheres were maintained in 0.01 M phosphate buffer, pH 7.4 at 37° C. and the residual naltrexone in the microspheres determined at the times indicated.

| Lot no. | Dog ID | Naltrexone loading, target wt % | Nalltrexone loading, actual wt % | Encapsulation efficiency, % | Temperature, ° C. | Polymer inherent viscosity, dl/g | Mean particle size, µm |
|---|---|---|---|---|---|---|---|
| 92 | 2062-HM<br>2067-HM<br>2073-IM | 50 | 38.3 | 77 | | 1.07 | 57.76 |
| 142 | 2063-JM<br>2066-JM<br>2070-KM | 50 | 42.5 | 85 | | 1.07 | 44.36 |
| 118[a] | 2065-FM<br>2072-FM<br>2075-GM | 60 | 49.0 | 82 | 22 | 1.07 | 39.78 |

| Lot no. | Naltrexone dose, mg | Microsphere dose | Vehicle, mL | Naltrexone in plasma ng/mL) (hrs) 1 hr | 2 hr | 4 hr | 8 hr | 24 hr | 48 hr |
|---|---|---|---|---|---|---|---|---|---|
| 92 | 165 | 430.8 | 1.8 | 6.8 | 2.79 | 1.82 | 0.73 | 0.82 | 0.81 |
| | 147 | 383.8 | 1.8 | 6.33 | 4.14 | 2.34 | 0.64 | | 0.86 |
| | 202.5 | 528.7 | 1.7 | 9.66 | 5.28 | 2.41 | 0.89 | 1.13 | 0.61 |
| 142 | 135 | 317.6 | 1.8 | 6.22 | 4.14 | 2.27 | 0.67 | 1.24 | 1.23 |
| | 165 | 388.2 | 1.8 | 5.19 | 3.5 | 2.33 | 0.68 | 0.72 | 1.04 |
| | 191.3 | 566.5 | 1.7 | 17.28 | 8.79 | 3.21 | 1.35 | 1.02 | 0.84 |
| 118 | 165 | 336.7 | 1.8 | 15.56 | 7.39 | | 1.25 | 1.81 | 1.8 |
| | 133.5 | 272.4 | 1.9 | 7.6 | 4.04 | 1.77 | 0.79 | 0.71 | 0.9 |
| | 225 | 459.2 | 1.8 | 13.02 | 6.62 | 3.2 | 1.02 | 1.41 | 1.28 |

| Lot no. | Naltrexone in plasma, ng/mL 3 day | 7 day | 11 day | 14 day | 18 day | 21 day | 29 day | 35 day |
|---|---|---|---|---|---|---|---|---|
| 92 | 1.17 | 24.95 | 5.14 | 3.99 | 3.27 | 3.63 | 1.38 | 0.7 |
| | 0.62 | 18.04 | 11.13 | 7.22 | 4.87 | 3.42 | 1.8 | 1.55 |
| | 1.29 | 40.1 | 17.71 | 7.74 | 4.43 | 4.2 | 1.26 | NA |
| 142 | 1.55 | 30.35 | 7.7 | 2.79 | 1.74 | 1.31 | 0.99 | 0.86 |
| | 1.03 | 23.3 | 5.82 | 2.38 | 2.1 | 2.15 | 1.46 | 0.87 |
| | 1.14 | 32.27 | 11.98 | 2.73 | 7.18 | 5.74 | 1.8 | NA |
| 118e | 2.44 | 45.3 | 7.17 | 4.65 | 1.22 | 0.48 | BQL | |
| | 1.02 | 28.4 | 1.98 | 0.71 | BQL | | | |
| | 2.21 | 35.01 | 5.63 | 2.07 | 1.44 | 0.54 | BQL | |

[a]continuous phase was at room temperature (22° C.) and water saturated with 3% ethyl acetate
BQL = Below quantitation level Analysis for Blood Levels in Dogs An analysis for naltrexone in dog plasma was developed using HPLC and electrochemical detection. Blank dog plasma was evaluated, as well as spiked plasma. No endogenous compounds present in the plasma, after sample extraction, interfere with the determination of naltrexone and the internal standard. The method was characterized for linearity, accuracy, precision, and sensitivity. The linear range of the method extends from 0.5 to 10 ng/mL of naltrexone in dog plasma. The precision is high with the percent difference between the theoretical and the back-calculated concentration of standards being less than 15%. The lower limit of detection is 0.5 ng/mL. All pharmacokinetics study samples in dogs were evaluated using this method.

The dogs were challenged with fentanyl to determine whether the response to fentanyl challenge was blunted by the naltrexone. At circulating levels of naltrexone <0.2 ng/mL, effects on canine respiration were observed at 0.01, 0.02 and 0.04 mg/kg fentanyl. When used intravenously, fentanyl produces the same EEG depression as 0.5–8 mg/kg morphine in conscious dogs. Successive opiate challenges were used and the increasing doses of opiate needed to produce a minimal response in untreated controls were identified weekly. The dose identified was then given to the slow release naltrexone treated dogs. Upon opiate challenge, the four parameters selected for monitoring were measured: pain aversion; alertness; respiratory rate and pupil diameter. Each successive treatment with fentanyl required higher doses for control dogs to reach alertness level 5. The first fentanyl dose was 50 µg and each week the successive doses were 60, 70, 110, 150, 180, 220, 240, and 280 µg.

The data for Formulation F-1 may be summarized as follows:

Summary of Opioid Challenge Study for Dogs Treated with Formulation F-1

| Type of Dog[1] | Dog Number | F-1 Lot Number | Days after dosing of the opioid challenge | Opioid, dose (mcg) | PUPIL SIZE, cm Pre | Post | ALERTNESS STATUS[2] Pre | Post | FLEXOR REFLEX[3] Pre | Post | Veterinarian Assessment |
|---|---|---|---|---|---|---|---|---|---|---|---|
| Control | 2521 | | | Fentanyl, 70 | 1.2 | 0.9 | 3 | 4 | + | D | suboptimal opioid dose used |
| Control | 2530 | | | Fentanyl, 70 | 1.2 | 0.9 | 3 | 3.5 | + | D | suboptimal opioid dose used |
| F-1 | 2520 | J437-041 | 1 | Fentanyl, 70 | 1.0 | 1.0 | 3 | 3 | + | + | full block |
| F-1 | 2503 | J437-041 | 1 | Fentanyl, 70 | 1.2 | 1.0 | 3 | 3 | + | + | full block |
| Control | 2521 | | | Fentanyl, 110 | 1.2 | 0.9 | 3 | 5 | + | D | full opioid response obtained |
| Control | 2530 | | | Fentanyl, 110 | 1.0 | 0.9 | 3 | 5 | + | D | full opioid responte obtained |
| F-1 | 2520 | J437-041 | 8 | Fentanyl, 110 | 1.0 | 0.9 | 3 | 3 | + | + | full block |
| F-1 | 2503 | J437-041 | 8 | Fentanyl, 110 | 1.4 | 1.2 | 3 | 3.5 | + | + | full block |
| Control | 2521 | | | Fentanyl, 187.5 | 1.2 | 0.9 | 3 | 5 | + | D, (−) | full opioid response obtained |
| Control | 2530 | | | Fentanyl, 175 | 1.0 | 0.8 | 3 | 5 | + | D, (−) | full opioid resposse obtained |
| F-1 | 2507 | J554-045 | 12 | Fentanyl, 180 | 1.0 | 0.9 | 3 | 4 | + | + | partial block |
| F-1 | 2518 | J554-045 | 12 | Fentanyl, 180 | 1.2 | 1.2 | 3 | 4 | + | D | partial block |
| Control | 2521 | | | Fentanyl, 150 | 1.2 | 0.9 | 3 | 5 | + | D | full opioid response obtained |
| Control | 2530 | | | Fentanyl, 150 | 0.9 | 0.8 | 3 | 5 | + | D | full opioid response obtained |
| F-1 | 2520 | J437-041 | 15 | Fentanyl, 150 | 1.0 | 1.0 | 3 | 4 | + | + | partial block |
| F-1 | 2503 | J437-041 | 15 | Fentanyl, 150 | 1.4 | 1.0 | 3 | 3 | + | + | partial block |
| Control | 2521 | | | Fentanyl, 225 | 1.2 | 1.0 | 3 | 5 | + | − | full opioid response obtained |
| Control | 2530 | | | Fentanyl, 215 | 1.0 | 0.9 | 3 | 5 | + | − | full opioid response obtained |
| F-1 | 2507 | J554-045 | 19 | Fentanyl, 220 | 1.2 | 1.0 | 3 | 4 | + | D | partial block |
| F-1 | 2518 | J554-045 | 19 | Fentanyl, 220 | 1.2 | 1.0 | 3 | 4 | + | D | partial block |
| Control | 2521 | | | Fentanyl, 250 | 1.2 | 0.9 | 3 | 5 | + | — | full opioid response obtained |
| F-1 | 2507 | J554-045 | 26 | Fentanyl, 240 | 1.0 | 0.8 | 3 | 4 | + | D | partial block |
| F-1 | 2518 | J554-045 | 26 | Fentanyl, 240 | 1.0 | 0.9 | 3 | 3 | + | — | partial block |
| Control | 2521 | | | Fentanyl, 280 | 1.2 | 0.9 | 3 | 5 | + | — | full opioid response obtained |
| Control | 2530 | | | Fentanyl, 280 | 1.0 | 0.9 | 3 | 5 | + | D | full opioid response obtained |
| F-1 | 2507 | J554-045 | 33 | Fentanyl, 280 | 1.0 | 0.9 | 3 | 4 | + | + | partial block |
| F-1 | 2518 | J554-045 | 33 | Fentanyl, 280 | 1.0 | 0.9 | 3 | 3 | + | + | partial block |
| Control | 2521 | | | Fentanyl, 187.5 | 1.2 | 0.9 | 3 | 5 | + | D, (−) | full opioid response obtained |
| Control | 2530 | | | Fentanyl, 175 | 1.0 | 0.8 | 3 | 5 | + | D, (−) | full opioid response obtained |
| F-1 | 2520 | J437-041 | 55 | Fentanyl, 180 | 1.0 | 1.0 | 3 | 4 | + | + | partial block |
| F-1 | 2503 | J437-041 | 55 | Fentanyl, 180 | 1.2 | 1.2 | 3 | 2 | + | + | partial block |
| Control | 2521 | | | Fentanyl, 225 | 1.2 | 1.0 | 3 | 5 | + | − | full opioid response obtained |
| Control | 2530 | | | Fentanyt, 215 | 1.0 | 0.9 | 3 | 5 | + | − | full opioid response obtained |
| F-1 | 2520 | J437-041 | 63 | Fentanyl, 220 | 1.0 | 1.0 | 3 | 4 | + | + | partial block |
| F-1 | 2503 | J437-041 | 63 | Fentanyl, 220 | 1.4 | 1.0 | 3 | 4 | + | − | partial block |
| Control | 2521 | | | Fentanyl, 250 | 1.2 | 0.9 | 3 | 5 | + | − | full opioid response obtained |
| F-1 | 2520 | J437-041 | 70 | Fentanyl, 240 | 1.0 | 0.9 | 4 | 4 | + | + | partial block |
| F-1 | 2503 | J437-041 | 70 | Fentanyl, 240 | 1.2 | 1.4 | 3 | 4 | + | + | partial block |
| Control | 2521 | | | Fentanyl, 280 | 1.2 | 0.9 | 3 | 5 | + | − | full opioid response obtained |
| Control | 2530 | | | Fentanyl, 280 | 1.0 | 0.9 | 3 | 5 | + | D | full opisoid response obtained |
| F-1 | 2520 | J437-041 | 77 | Fentanyl, 280 | 1.0 | 0.8 | 3 | 4 | + | + | partial block |
| F-1 | 2503 | J437-041 | 77 | Fentanyl, 280 | 1.2 | 1.0 | 3 | 5 | + | D | minimal block |

NOTES:
[1]Control indicates Control dogs that were not treated with naltrexone.
F-1 indicates dogs that were dosed with 15 mg/kg naltrexone microspheres, Formulation F-1
[2]KEY: Alertness Status Scale
1 Agitated
3 Awake (standing)
3.5 Can stand but prefers to sit
4 Drowsy but Sitting
5 Recumbent
KEY: Flexor Reflux Scale
+ positive reflex
D depressed reflux
− no reflux The next study employed human subjects to determine their response to different protocols for administration and the naltrexone release profile of a number of different formulations.

Human Bioavailabilty and Safety in Volunteers
Dosing Schedule (mg of microencapsulated naltrexone in 2 or 4 mL of injection vehicle)

| Formulation | Group 1 | Group 2 | Group 3 | Group 4 | Group 5 | Group 6 |
|---|---|---|---|---|---|---|
| F-1 | 150 mg/2 mL | 300 mg 2 × 2 mL | 300 mg in 4 mL | — | 300 mg 2 × 2 mL | — |
| F-2 | 150 mg/2 mL | 150 mg/2 mL | — | — | — | — |
| F-3 | 150 mg/2 mL | 150 mg/2 mL | — | 4 mL | — | — |
| F-4 | 150 mg/2 mL | 150 mg/2 mL | — | 300 mg in — | — | — |
| F-1' | — | — | — | — | — | 150 mg/2 mL |

The microspheres were prepared as described above in accordance with FDA standards for human use. All reactants and products were analyzed to ensure that the batches had the proper composition, were not pyrogenic and could be used in humans. Both naltrexone and 6β-naltrexol were analyzed in patients using HPLC/MS. Naloxone was used as an internal standard and plasma samples were extracted into ethyl ether. Five standard curves were assayed over a 4-day period. Interday and intraday reproducibility, reinjection stability, benchtop stability, freeze/thaw stability, refrigeration stability and storage stability for up to 4 days at −20° C. were determined. Linearity was established for naltrexone between 0.50 and 50 ng/mL, and for 6β-naltrexol, between 2 and 100 ng/mL. The limits of quantitation for naltrexone and 6β-naltrexol were 0.50 ng/mL and 2.0 ng/mL, respectively. Precision/accuracy, and specificity were also measured.

The six formulations employed had the following designations and compositions:

F-1 Poly(D,L-lactide) (inherent viscosity of 0.37 dL/g) polymer with 25% target loading (actual loading 17±3%) of naltrexone F-1' Poly(D,L-lactide) (inherent viscosity of 0.37 dL/g) polymer with 50% target loading (actual loading 38%) of naltrexone F-2 Poly(D,L-lactide) (inherent viscosity of 1.07 dL/g) polymer with 50% target loading (actual loading 40±3%) of naltrexone F-3 50:50 combination of F-1 and F-2 microspheres (by weight of naltrexone)

F-4 90:10 combination of poly(D,L-lactide) as that use in F-1 and F-2, respectively, with 50% target loading (actual loading 40±3%) of naltrexone Size distribution was such that 90 volume % of each batch is >50 μm and <70 μm Analysis for Blood Levels from Clinical Samples An analysis for naltrexone and 6β-naltrexol in human plasma was developed using HPLC/MS. Naloxone was used as an internal standard and plasma samples were extracted into ethyl ether. Five standard curves were assayed over a 4-day period. Interday and intraday reproducibility, reinjection stability, benchtop stability, freeze/thaw stability, refrigeration stability and storage stability for up to 4 days at −20° C. were determined. Linearity was established for naltrexone between 0.50 and 50 ng/mL, and for 6β-naltrexol, between 2 and 100 ng/mL. The limits of quantitation for naltrexone and 6β-naltrexol were 0.50 ng/mL and 2.0 ng/mL, respectively. Precision/accuracy, and specificity were also measured. All human clinical pharmacokinetics study samples were evaluated using this method.

Examination of the AUC data for Formulation F-1' was based on extrapolating the AUC data from single 50-mg tablets dosed on one day to that expected if one tablet was taken daily, over a 31-day period. This was contrasted with the AUC values from the group of 5 subjects (Group 3) receiving 300 mg of microencapsulated naltrexone in microspheres Formulation F-1' in a single 4-mL injection with plasma concentration data measurable for 31 days.

Mean AUC levels for naltrexone and 6β-naltrexol are tabulated below by oral versus F-1. Group 3 treatment.

| | All Groups Tablet (50 mg) | | F-1 Group 3 F-1 (300 mg) in 4 mL | | Ratio |
|---|---|---|---|---|---|
| | $AUC_{0-24h}$ [μg·L$^{-1}$·h] | $AUC_{0-32d}$ (Extrapolated) [μg·L$^{-1}$·h] | $AUC_{0-32d}$ [μg·L$^{-1}$·h] | % dev | F-1/ Tablets |
| Naltrexone | | | | | |
| Mean | 27.8 | 888.0 | 1051.6 | 118.3 | 1.18 |
| Minimum | 4.5 | 144.8 | 419.8 | | 2.90 |
| Maximum | 99.2 | 3173.0 | 2384.29 | | 0.75 |
| 6β-Naltrexol | | | | | |
| Mean | 610.1 | 19521.9 | 3663.9 | 18.8 | 0.47 |
| Minimum | 402.4 | 12876.8 | 1202.7 | | 0.09 |
| Maximum | 985.0 | 31521.2 | 9240.9 | | 0.29 |

Naltrexone
Mean ratio is 1.18 (range 0.75 to 2.9)
6β-Naltrexol
Mean ratio is 0.17 (range of 0.09 to 0.29)

The data indicate that the exposure to the active naltrexone moiety is likely to be comparable whether taking daily 50-mg tablets for one month or one 300-mg of microencapsulated naltrexone by intramuscular injection of microsphere Formulation F-1' once monthly.

The overall pharmacokinetic parameters of the F-1' formulation and the tablets are summarized in the following table:

Summary of mean ± SD Pharmacokinetic Parameters

|  | F-1' 300 mg IM | | TABLETS 50 mg peroral | |
|---|---|---|---|---|
|  | NAL | 6-β METAB | NAL | 6-β METAB |
| $T_{max}$, hr | 106.8 ± 147.5 | 380 ± 266.6 | 1.3 ± 0.7 | 1.4 ± 0.7 |
| $C_{max}$ | 6.1 ± 4.6 | 15.6 ± 14.2 | 7.7 ± 6.5 | 69.8 ± 27.2 |
| $T_{LAST}$, hr | 768 ± 0 | 768 ± 0 | 8.9 ± 4.8 | 24.0 ± 0 |
| $C_{LAST}$ | 0.71 ± 0.32 | 2.82 ± 1.38 | 0.97 ± 0.46 | 12.07 ± 5.32 |
| $AUC_{0-LAST}$ | 1051.6 ± 792.6 | 3663.9 ± 3196 | 27.8 ± 22.5 | 610.1 ± 151.4 |

The pharmacokinetic parameters for the individual subjects receiving F-1 are summarized below:

Microsphere Formulation F-1 (Naltrexone data)

|  | 150 mg naltrexone in 2 mL vehicle | 300 mg naltrexone in 2 × 2 mL vehicle | 300 mg naltrexone in 4 mL vehicle | | | | |
|---|---|---|---|---|---|---|---|
| $C_{max}$, ng/mL | 1.8 | 7.9 | 3.5 | 3.5 | 14.1 | 6.1 | 3.3 |
| $T_{max}$, hr | 504 | 31.2 | 4 | 1 | 312 | 216 | 1 |
| $C_{Day\ 31}$, ng/mL | 0.7 | 0.4 | 0.7 | 0.9 | 0.8 | 0.2 | 1.0 |

Overall the plasma concentrations of F-1' exhibit an initial maximum between one and four hours and a second maximum during Week 2–3. It is likely that the initial peak reflects naltrexone on or near the surface of the microspheres readily available upon injection. Once injected the microspheres imbibe fluids which forms pores through which the naltrexone dissolves to maintain continuous delivery of drug. The second peaks during weeks 2–3 are reflective of the biodegradation of the microspheres and the probability that the initial mass is disintegrating creating a greater surface area of exposed naltrexone at the depot site with a temporal increase in naltrexone plasma concentrates. The continuous release of naltrexone during the one-month interval following dosing maintains the driving force of drug from the depot injection site through the bloodstream to the opioid receptor. This driving force will ensure receptor blockade for the one-month dosing interval.

Examination of Area Under the Curve data for Formulation F-1' indicates continuous release of drug over one month and fairly comparable exposure of naltrexone whether taking a 300 mg once monthly injection or 50 mg orally once daily.

The data may be characterized as follows. The AUC after a single 50-mg tablet was extrapolated to 32 days based on the assumption that the usual dose in the therapy of addiction is 50 mg/day. Additionally the assumption that there is no difference between the pharmacokinetic profiles of naltrexone and its metabolite after single and multiple doses as demonstrated in previous clinical studies is used. After F-1' injection, the $AUC_{0\text{-}32day}$ is similar to that after 32 daily 50-mg oral doses. Metabolite exposure after oral doses is 22-fold higher than naltrexone exposure. The ratio for metabolite/naltrexone exposure is 3.5 for F-1'. $T_{last}$ after oral dosing is an average 8.9 hr. With the sustained-release formulations, there is a constant presence of naltrexone in plasma in the effective concentration range.

Additional data are set forth in the following table and the accompanying figures.

| Microsphere Formulation | Number of subjects | Dose, mg naltrexone | $AUC_{0-31d}$ [μg · L⁻ · h] | $AUC_{0-inf}$ [μg · L⁻ · h] | Ratio, % |
|---|---|---|---|---|---|
| F-1 | 11 | 300 | 1160 ± 689 | 1712 ± 462 | 67 |
| F-2 | 2 | 150 | 970 | 1002 | 97 |
| F-3 | 2 | 150 | 471 | 623 | 76 |
| F-4 | 5 | 300 | 1632 ± 213 | 1982 ± 194 | 82 |
| F-1' | 5 | 150 | 750 ± 294 | 868 ± 215 | 86 |

$AUC_{0-31}$ vs $AUC_{0-inf}$

The above table shows that the release of the naltrexone over the 31-day period is a major proportion of the total amount of naltrexone initially injected.

It is evident from the above results that a long-term supply of naltrexone at a physiologically effective concentration can be provided in vivo. In this way, compliance problems associated with the requirement of taking a pill daily can be avoided. Monitoring to determine whether the subject has taken the daily pill is obviated. The subject is better able to deal with the problem of substance abuse, being aware that the subject has better control in the case of alcoholism and will not obtain the desired euphoria from heroin. Counseling can be more effectively performed, since the subject will be discouraged from taking heroin and in the case of alcoholism, will be better able to cope with fewer drinks. In this way, subjects will be able to function and fulfill their obligations to their families and society.

Slow-release naltrexone according to this invention reduces concerns with hepatotoxicity associated with the 6β-naltrexol metabolite. By avoiding the high first pass metabolism with a daily dose and maintaining a constant lower supply of naltrexone, the levels of 6β-naltrexol are reduced. Also, the high first pass metabolism resulting from the initial high concentration of naltrexone when taking a tablet daily is avoided. Less naltrexone need be administered, reducing the amount of drug required for maintenance of the human subject over a one-month period.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A microsphere composition comprising:
   a naltrexone free base in an amount in the range of 15 to 50 weight %;
   a poly(D,L-lactide) as a matrix;
   a residual amount of ethyl acetate that is less than about 3 weight %, wherein said composition is capable of providing over a period of at least 28 days a physiologically effective level of naltrexone to reduce the consumption of at least one of heroin and alcohol when administered intramuscularly in a mammal, and wherein at least 90 weight % of said microsphere composition comprises microspheres having a diameter in the range of 20 to 100 µm.

2. A microsphere composition comprising:
   a naltrexone free base in an amount in the range of 15 to 25 weight %;
   a poly(D,L-lactide) as a matrix, wherein said poly(D,L-lactide) has an inherent viscosity in the range of about 0.3 to 0.4 dL/g;
   less than about 3 weight % ethyl acetate, wherein said composition is capable of providing over a period of at least 28 days a physiologically effective level of naltrexone to reduce the consumption of at least one of heroin and alcohol when administered intramuscularly in a mammal, and wherein at least 90 weight % of said microsphere composition comprises microspheres having a diameter in the range of 20 to 100 µm.

3. A microsphere composition comprising:
   a naltrexone free base in an amount in the range of 35 to 45 weight %;
   a poly(D,L-lactide) as a matrix, wherein said poly(D,L-lactide) has an inherent viscosity in the range of about 1.0 to 1.1 dL/g;
   less than about 3 weight % ethyl acetate, wherein said composition is capable of providing over a period of at least 28 days a physiologically effective level of naltrexone to reduce the consumption of at least one of heroin and alcohol when administered intramuscularly in a mammal, and wherein at least 90 weight % of said microsphere composition comprises microspheres having a diameter in the range of 20 to 100 µm.

4. The microsphere composition according to claim 1, wherein said microspheres are coated with mannitol.

5. The microsphere composition according to claim 1, wherein said poly(D,L-lactide) is a mixture of poly(D,L-lactide) of differing inherent viscosities.

6. The microsphere composition according to claim 1, wherein said composition is a mixture of microspheres which differ in at least one of weight % of naltrexone or poly(D,L-lactide) of differing inherent viscosity.

7. The microsphere composition according to claim 1, wherein said microspheres are prepared by introducing a solution of said naltrexone and poly(D,L-lactide) in ethyl acetate into an aqueous solution of poly(vinyl alcohol), isolating the resulting microspheres by extracting the ethyl acetate with water.

8. A microsphere composition comprising:
   35 to 45 weight % naltrexone having a poly(D,L-lactide) matrix wherein said composition is capable of releasing about 10 to 40% per week of the initial amount of said naltrexone in said microsphere composition into a human subject over a 4-week period, while maintaining a therapeutic dosage of at least about 1 ng/mL during said 4-week period.

9. The microsphere composition according to claim 8, wherein during only one week of said 4-week period is greater than about 20% of the initial amount of said naltrexone released.

10. A formulation for injection comprising:
    a microsphere composition according to claim 1 or claim 8;
    carboxymethyl cellulose; and
    mannitol.

11. A syringe comprising a formulation according to claim 10.

12. A method for reducing the consumption of at least one of heroin and alcohol by a subject abusing at least one of heroin and alcohol, said method comprising:
    administering intramuscularly an effective dose of a microsphere composition according to claim 1 in an amount sufficient to inhibit the consumption of heroin and alcohol, whereby the consumption of at least one of heroin and alcohol is reduced.

13. The method according to claim 12, wherein said administering comprises a sample of from 2 to 4 mL.

14. A method for reducing the consumption of at least one of heroin and alcohol by a subject abusing at least one of heroin and alcohol, said method comprising the steps of:
    providing said subject with an initial dose of a microsphere composition according to any one of claims 1–3, wherein said initial dose continues to release naltrexone at a concentration of at least an effective level for greater than 28 days after applying said initial dose;
    prior to the concentration of naltrexone in said subject falling below said effective level, administering an additional dose of said microsphere composition, wherein the combination of the remaining portion of said initial dose and said additional dose provides naltrexone at a concentration of at least said effective level for at least an additional 28 days after administrating said additional dose; and
    injecting another dose of said microsphere composition, wherein the combination of the remaining portion of said additional dose of said microsphere composition and said another dose of said microsphere composition maintains said concentration of naltrexone above said effective level for at least another 28 days after injecting said another dose.

15. The method according to claim 14, wherein said administering comprises a sample of from 2 to 4 mL.

16. A method for reducing the consumption of at least one of heroin and alcohol by a subject abusing at least one of heroin and alcohol, said method comprising:

administering intramuscularly an effective dose of a microsphere composition according to claim 8 in an amount sufficient to inhibit the consumption of heroin and alcohol, whereby the consumption of at least one of heroin and alcohol is reduced.

17. A method of making a plurality of naltrexone poly(D,L-lactide) microspheres, said method comprising:

preparing an approximately 2 to 7 weight % poly(D,L-lactide) polymer solution with ethyl acetate as the solvent;

combining naltrexone free base with said polymer solution to produce a naltrexone dispersed phase containing approximately 2 to 3 weight % naltrexone;

preparing approximately a 2 weight % of poly(vinyl alcohol) solution in water and adding ethyl acetate to produce a poly(vinyl alcohol) continuous phase;

combining said naltrexone dispersed phase with said polyvinyl alcohol continuous phase to produce an emulsion that contains microdroplets comprising naltrexone, ethyl acetate and poly(D,L-lactide); and contacting said emulsion with an extraction water phase whereby said plurality of naltrexone poly(D,L-lactide) microspheres are obtained.

18. The method according to claim 17, further comprising separating said microspheres from said extraction water phase.

19. Naltrexone poly(D,L-lactide) microspheres produced according to the method of claim 17.

20. Naltrexone poly(D,L-lactide) microspheres produced according to the method of claim 18.

21. A method of microencapsulating naltrexone with poly(D,L-lactide) to form naltrexone poly(D,L-lactide) microspheres, said method comprising preparing approximately a 2 to 7 weight % of poly(D,L-lactide) polymer solution with naltrexone free base and ethyl acetate as the solvent;

preparing approximately a 2 weight % of poly(vinyl alcohol) solution in water and adding ethyl acetate to produce a poly(vinyl alcohol) continuous phase;

combining said polymer solution with said poly(vinyl alcohol) continuous phase so that an emulsion which contains microdroplets comprising naltrexone, poly(D,L-lactide) and ethyl acetate is obtained; and contacting said emulsion with an extraction water phase whereby said naltrexone poly (D,L-lactide) microspheres are obtained.

22. The method according to claim 21, further comprising separating said naltrexone poly(D,L) microspheres from said extraction water phase.

23. Naltrexone poly(D,L-lactide) microspheres produced according to the method of claim 21.

24. Naltrexone poly(D,L-lactide) microspheres produced according to the method of claim 22.

25. A kit for reducing the consumption of at least one of heroin and alcohol by a subject abusing at least one of heroin and alcohol, said kit comprising a microsphere composition according to claim 1 or claim 8 in a vial.

26. The kit according to claim 25, further comprising a diluent containing mannitol and carboxymethyl cellulose.

* * * * *